(12) United States Patent
Simon et al.

(10) Patent No.: US 7,709,812 B2
(45) Date of Patent: May 4, 2010

(54) ULTRAVIOLET RADIATION MONITORING DEVICE AND A METHOD OF USING THE SAME

(75) Inventors: Barrington L. Simon, 717 Woodhaven Place, Ancaster, Onatario (CA) L9G 5B1; Robert G. Dickie, Newmarket (CA)

(73) Assignee: Barrington L. Simon, Ancaster, Ontario (CA)

( * ) Notice: Subject to any disclaimer, the term of this patent is extended or adjusted under 35 U.S.C. 154(b) by 223 days.

(21) Appl. No.: 11/701,052

(22) Filed: Feb. 1, 2007

(65) Prior Publication Data

US 2008/0185534 A1    Aug. 7, 2008

(51) Int. Cl.
*G01N 21/00* (2006.01)
*G03B 11/00* (2006.01)

(52) U.S. Cl. .................. 250/474.1; 250/482.1
(58) Field of Classification Search ............... 250/474.1, 250/482.1
See application file for complete search history.

(56) References Cited

U.S. PATENT DOCUMENTS

| | | |
|---|---|---|
| 3,787,687 A | 1/1974 | Trumble |
| 3,903,423 A | 9/1975 | Zweig |
| 4,829,187 A | 5/1989 | Tomita et al. |
| 5,008,548 A | 4/1991 | Gat |
| 5,117,116 A | 5/1992 | Bannard et al. |
| 5,151,600 A | 9/1992 | Black |
| 5,612,541 A | 3/1997 | Hoffmann et al. |
| 5,986,273 A | 11/1999 | Tripp et al. |
| 6,060,321 A | 5/2000 | Hovorka |
| 6,132,681 A | 10/2000 | Faran et al. |
| 6,504,161 B1 | 1/2003 | Jackson et al. |
| 6,818,904 B1 | 11/2004 | Ferren et al. |

*Primary Examiner*—David P Porta
*Assistant Examiner*—Carolyn Igyarto
(74) *Attorney, Agent, or Firm*—Sand & Sebolt (57) ABSTRACT

A disposable device for monitoring exposure to ultraviolet radiation (UVR) over a single period of time and a cumulative period of time. The device includes a base upon which is applied a UVR sensitive material that irreversibly changes after exposure to UVR. A protective covering is applied over the UVR sensitive material and includes segments that are individually removable to reveal a portion of the UVR sensitive material thereunder. A UVR exposure scale and first and second keys are provided on the base. A first segment of the covering is removed and the base is placed in an appropriate location. After a period of time, the change in the UVR sensitive material is compared to the scale and first key to determine if the level of exposure is safe for that time period. The procedure may be repeated over a number of time periods with a new segment of the protective covering being removed for each time period. The cumulative UVR exposure is determined by comparing the change in the first time period's UVR sensitive material to the scale and a second key associated therewith.

20 Claims, 7 Drawing Sheets

ULTRAVIOLET RADIATION MONITORING DEVICE AND A METHOD OF USING THE SAME

BACKGROUND OF THE INVENTION

1. Technical Field

This invention generally relates to health products. More particularly, the invention relates to a monitoring device. Specifically, the invention relates to a device that aids in monitoring exposure to ultraviolet radiation (UVR) which includes a UVR sensitive material and a cover tape that are progressively removed to reveal the UVR sensitive material over a period of time.

2. Background Information

Over the past several decades, there has been a growing awareness of the dangers of overexposure of the skin to ultraviolet radiation from the sun. The climbing rates of skin cancers, awareness of problems with the ozone layer and media attention to these and other issues have made the general population more aware of the need to take preventive steps to protect their skin from potential damage. Some of these measures have included using specially manufactured UV blocking clothing, wearing of hats and sunglasses, and the application of sunblocks and sunscreens that contain protective chemicals.

All of these measures restrict the amount of UV radiation a person is exposed to. They do not, however, provide any real information about the actual quantity of UV radiation a person is receiving and whether or not that exposure level is safe.

There are several products available today that may be used to monitor a person's exposure to UVR. An example of such a device is found in U.S. Pat. No. 5,117,116 issued to Bannard et al, discloses a UV radiation detection device that is applied to the skin by way of an adhesive. The device comprises a housing having a UV sensitive material applied to an inner surface thereof. The top of the housing shields the UV sensitive material from direct exposure to UV radiation. When the UV sensitive material is exposed to indirect UV radiation that has been reflected off the individual's skin, the material irreversibly changes color. The color change is compared to a graduated scale to determine if the level of exposure is harmful. The device is designed for single day use and is disposable. One of the issues with this type of device is that attaching the device on the skin may leave a shaped area that has not been as exposed to the sun as the surrounding region. This leaves a less tanned shaped region on the body which some individuals find aesthetically displeasing. Furthermore, the device is intended as a single use device and consequently is of no assistance for monitoring cumulative exposure to UVR over a period of time.

Yet another device is disclosed in U.S. Pat. No. 6,132,681 issued to Faran et al. The device is contemplated to be in the form of a sticker or badge that is attachable to the individual or to their clothing, for example. The device is manufactured to indicate when a specific quantity of exposure has occurred, namely 1 MED. The patent defines a MED as "the radiant exposure of the UV radiation that produces a just noticeable erythema (i.e., sunburn) on previously unexposed skin." (Clarification added by the applicant). The device includes photochromic compounds which irreversibly change their color after exposure to this 1 MED dose of UVR and once this irreversible change has occurred, the individual is supposed to get out of the sun and throw away the device. The device takes into account the fact that individuals have differently pigmented skin and a 1 MED dose of UVR for a fair skinned individual differs greatly from a 1 MED does for a darker skinned individual. Consequently a number of differently graduated devices would be made available and the individual will purchase the device most appropriate for their skin color. The device does not include a graduated scale that indicates a range of possible exposures to UV radiation—just a single color change when the full dose of radiation has been received. This device again may leave a less tanned region on the person's body and is only meant for single use and is therefore of little assistance in monitoring UVR exposure over several days.

Finally, Hovorka discloses in U.S. Pat. No. 6,060,321 a disposable UV dosimeter that has a test zone that changes color when exposed to UVR over a period of time. The test zone is surrounded by a color panel which includes at least three areas that indicate whether the individual has been exposed to a low, moderate or high dose of UVR. The user compares the test zone with the color panel to determine the level of UVR to which they have been exposed.

These and numerous other devices have been developed for determining the level of an individual's exposure to UVR. However, these devices have been designed for single day use. Most vacationers tend to go to sunny destinations for an average a length of about a week. The daily exposure to the human skin is cumulative over this length of time. Each day can have varying amounts of sun intensity and the user may or may not be exposing themselves to the sun each day or part of the day.

A number of other UV monitoring devices which include complex electronic circuits, display panels and the like, have been proposed for monitoring exposure to UVR over a period of time. These devices are not contemplated to be disposable, would typically be relatively expensive and may be prone to failure because of all their component parts.

Accurate monitoring of the sun's intensity on humans is problematic as humans are three-dimensional in nature. They therefore tend to have different parts of their body exposed to the sun at different times and at different rates. The angle of the sun to the monitoring device has a large effect on how much exposure the card will record. There are also two different types of possible users of UVR monitoring devices. A responsible adult will use the device to monitor their personal exposure and will likely place the device correctly for exposure to the sun. When they are in the sun, they will monitor the device throughout the period and decide if the exposure is excessive. The other type of user would be a person who is taken care of a group of children in a common area such as a park or swimming pool. Each of these applications requires a different device for monitoring UVR exposure.

It would be therefore be desirable to have a UV monitoring device that would last the duration of a typical vacation, i.e., one week, and which would provide both daily and weekly readings of UVR exposure. The daily reading is important so that the individual can ensure they are not being exposed to too much UVR from the sun in one single day. The weekly cumulative readings are important so as to monitor the total sun exposure received during a week's vacation.

SUMMARY OF THE INVENTION

The present invention comprises a disposable device for monitoring exposure to UVR (UVR) over a single period of time and a cumulative period of time and a method of monitoring UVR exposure. The device includes a base upon which is applied a UVR sensitive material that irreversibly changes after exposure to UVR. A protective covering is applied over the UVR sensitive material and includes tape segments that are individually removable to reveal a portion of the UVR sensitive material thereunder. A UVR exposure scale and key are provided on the base. A first segment of the covering is removed and the base is placed in an appropriate location. After a period of time, the change in the UVR sensitive material is compared to the scale and first part of the key to determine if the level of exposure is safe for that time period. The procedure may be repeated over a number of time periods with a new segment of the protective covering being removed for each time period. The cumulative UVR exposure is determined by comparing the change in the first time period's UVR sensitive material to the scale and a second part of the key.

BRIEF DESCRIPTION OF THE DRAWINGS

The preferred embodiments of the invention, illustrative of the best mode in which applicant has contemplated applying the principles, are set forth in the following description and are shown in the drawings and are particularly and distinctly pointed out and set forth in the appended claims.

DETAILED DESCRIPTION OF THE INVENTION

Referring to FIGS. 1-6, there is shown an ultraviolet radiation (UVR) monitoring device in accordance with the present invention, and generally indicated at 10. Monitoring device 10 comprises a card 12 that is of the shape and size of a credit card so that it may be easily and conveniently carried in a wallet or purse. Card 12 has a front surface 12a and a rear surface 12b.

Figure 1:
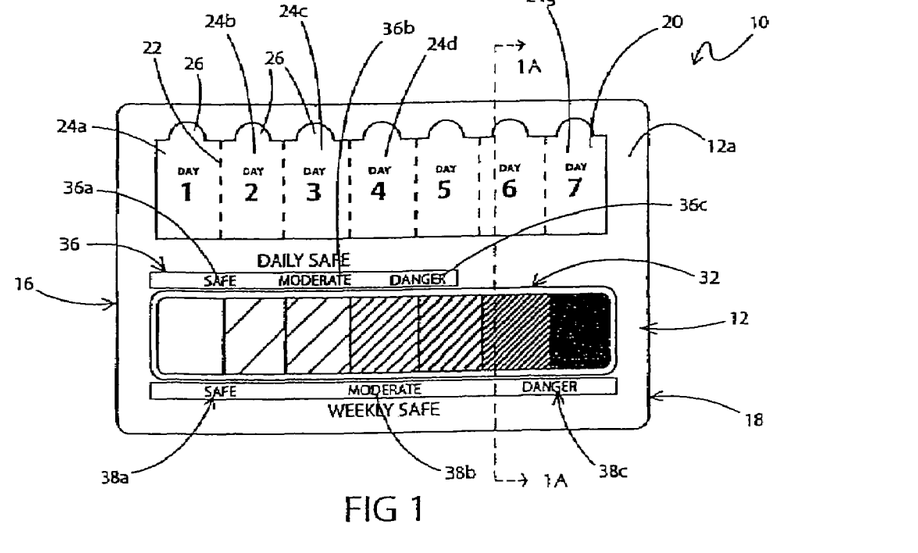
FIG. 1 is a front view of an ultraviolet radiation monitoring device in accordance with the present invention shown in an unused state.
Figure 1A:
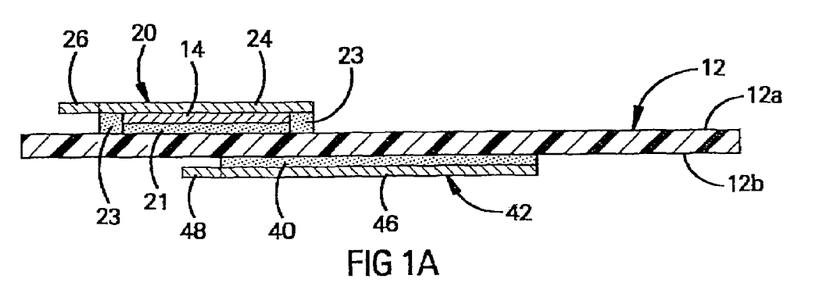
FIG. 1A is a cross-sectional view of the ultraviolet radiation monitoring device taken through line 1A-1A of FIG. 1.
Figure 1B:
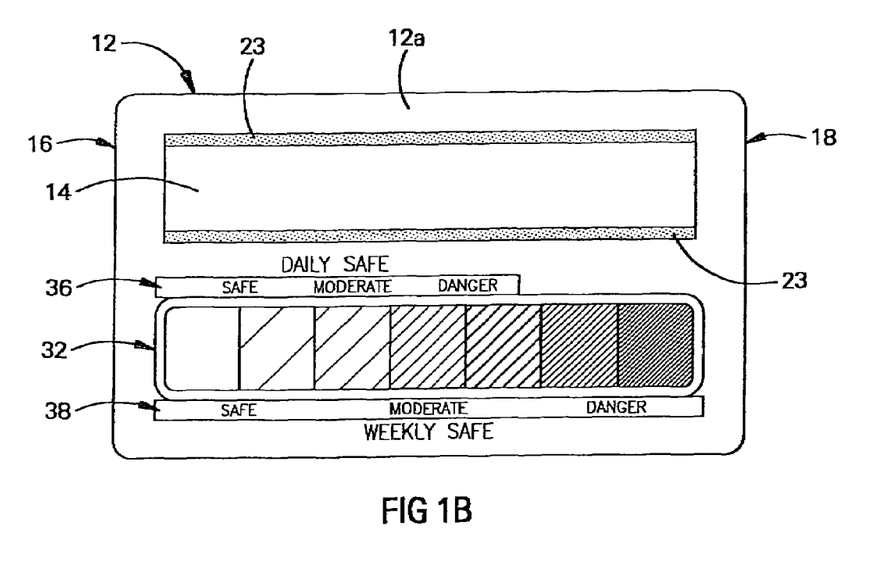
FIG. 1B is a front perspective view of the monitoring device with the protective strip removed to show the UVR sensitive material and the adhesive bands that secure the protective strip to the device.

In accordance with a specific feature of the present invention, a strip 14 of an ultraviolet sensitive material is secured to card 12 by an adhesive layer 21. The ultraviolet sensitive material may be of any suitable type known in the art that will react to UVR and will change color accordingly. The type of UV sensitive material used in strip 14 preferably changes color cumulatively and irreversibly. Strip 14 preferably is of a fairly substantial length extending from proximate a first side edge 16 of card 12 to proximate a second side edge 18 thereof.

In accordance with another specific feature of the present invention, a cover tape 20 is applied over the UV sensitive strip 14 to initially entirely prevent strip 14 from being exposed to UVR. Cover tape 20 preferably is made from a single length of paper. Cover tape 20 is provided with a plurality of lines of perforations 22 that effectively divide strip 20 into a plurality of individual segments 24, such as segments 24a, 24b-24g. An adhesive 23 is applied to an inner surface of cover tape 20 in such a manner that each segment 24 of strip 20 is individually secured to card 12. Segments 24 are also each provided with a tab 26 that enables it to be individually detached from strip 20 and removed from card 12. Tab 26 does not have an adhesive applied to an inner surface thereof and is therefor easy to grasp. When one segment, such as segment 24a is detached from cover tape 20, then segments 24b-24g remain fully secured to card 12 and prevent the portion of strip 14 disposed thereunder from being exposed to UVR. Segments 24 are also preferably marked with indicators 28 which identify the individual time segments represented by segments 24. So, for example, segment 24a is marked with an indicator 28 which reads "Day 1"; segment 24b is marked with an indicator 28 which reads "Day 2", and so on. Furthermore, card 12 preferably is also marked with indicators 30 that correspond to the indicators 28 on the individual segments. So, for example, the indicator 30 positioned on card 12 that is disposed underneath segment 24a is marked with an indicator 30 reading "1"; and the area under segment 24b is marked with the indicator 30 reading "2".

In accordance with yet another feature of the present invention, card 12 is also provided with an exposure scale 32. Scale 32 includes a plurality of permanently marked exposure indicators 34, such as indicators 34a, 34b through 34g. These indicators 34 are graduated to show increasing increments of UVR exposure. Indicator 34a is substantially clear showing little to no UVR exposure. Indicator 34b is hatched to show a smaller quantity of UVR exposure and finally indicator 34g is a solid color indicating maximum UVR exposure. Indicator scale 32 may be produced as a printed color scale that reflects the potential color changes that can occur in the ultraviolet sensitive strip 14 upon exposure to UVR. Alternatively, each individual indicator 34 of scale 32 may be produced using an ultraviolet sensitive material, such as the material used for strip 14. These individual pieces of UV sensitive material are exposed to a predetermined amount of UVR so that the irreversible color change occurs and then the scale 32 is produced by mounting the changed pieces of UV sensitive material on card 12.

Scale 32 is also provided with a first key 36 and a second key 38 for interpreting the level of exposure indicated by the single scale 32. First key 36 includes a plurality of first characters which indicate the safety of a daily level of UVR. So, for instance character 36a represents a low or "Safe" daily UVR exposure level to UVR, character 36b represents a "Moderate" daily exposure level and character 36c represents a high or daily exposure level to UVR and thus is indicated by the word "Danger".

Second key 38 is also used in conjunction with scale 32 and includes a second plurality of characters which represent cumulative exposure to UVR over a period of several days, and typically one week. So, for instance, character 38a represents a low or "Safe" cumulative weekly exposure level to UVR, character 38b represents a "Moderate" cumulative weekly exposure level and character 38c, "Danger", represents a high cumulative weekly exposure level.

Figure 3:
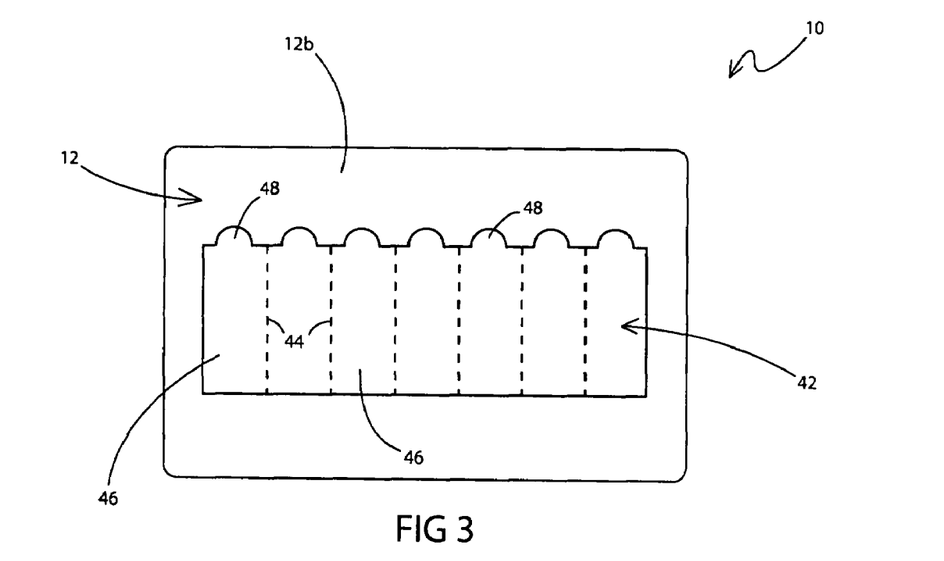
FIG. 3 is a rear view of the monitoring device of FIG. 1 showing a first manner of securing the device to an appropriate surface.
Figures 3A, 3B:
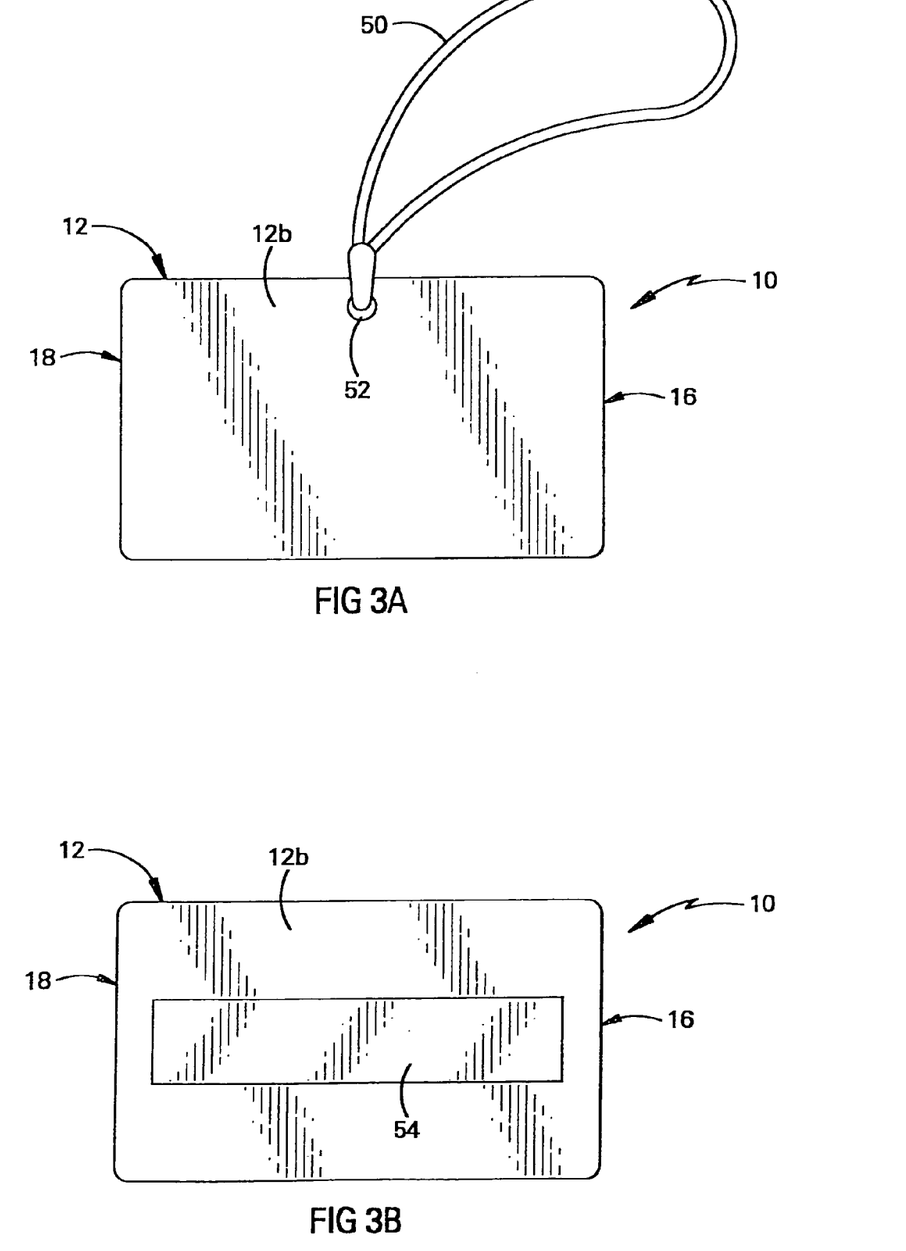
FIG. 3A is a rear view of the monitoring device showing an alternative manner of securing the device to an appropriate surface.
FIG. 3B is a rear view of the monitoring device showing a second alternative manner of securing the device to an appropriate surface.
Figure 4:
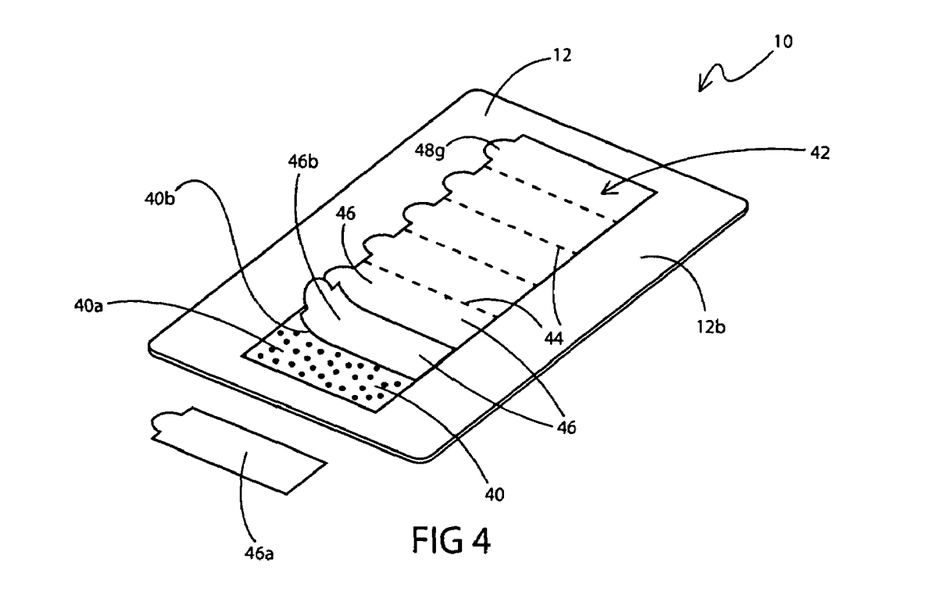
FIG. 4 is a rear perspective view of the monitoring device of FIG. 3.

Referring to FIGS. 3 & 4, card 12 includes an adhesive layer 40 on back surface 12b thereof. Adhesive layer 40 is covered with a paper strip 42 that is similarly manufactured to cover 20 on front 12a of card 12. Paper strip 42 includes a plurality of lines of perforations 44 that separate strip 42 into a plurality of individual sections 46. Each section 46 includes a tab 48 that is not in contact with adhesive layer 40 and that therefore may be easily grasped to remove the relevant section 46, such as 46a, from back 12b of card 12.

Referring to FIGS. 1-6, monitoring device 10 is used in the following manner. Device 10 is designed for monitoring an individual or group of individuals in an area where people are in the sun such as a group of children at a beach or pool party. The monitoring individual removes a first section 46a of the paper strip 42 from back surface 12b of card 12. This exposes a first region 40a of adhesive layer 40. Card 12 is then secured to an appropriate surface such as a beach umbrella, chair arm or any other convenient and properly exposed surface using adhesive region 40a. The monitoring individual also removes the first segment 24a of cover tape 20 on front surface 12a of card 12. This exposes a first region 14a of the UVR sensitive strip 14 on front surface 12a. The monitoring individual will check card 12 periodically and will compare the color change in region 14a with the indicators 34 on graduated scale 32. Region 14a represents the UVR exposure for the first day of that group or individual to the sun. Consequently, the monitoring individual will compare the color change in region 14a with the indicators 34 on scale 32, in conjunction with the first characters of first key 36, to determine whether the color change in region 14a is low, moderate or high. If the color change in region 14a is found to be low, the group can remain outdoors for a longer time period. If the color change in region 14a is found to be moderate, the group of children can be warned that their time outdoors is coming to an end. If the color change in region 14a is found to be high, then the monitoring individual knows it is time for the group to head indoors.

Figure 2:
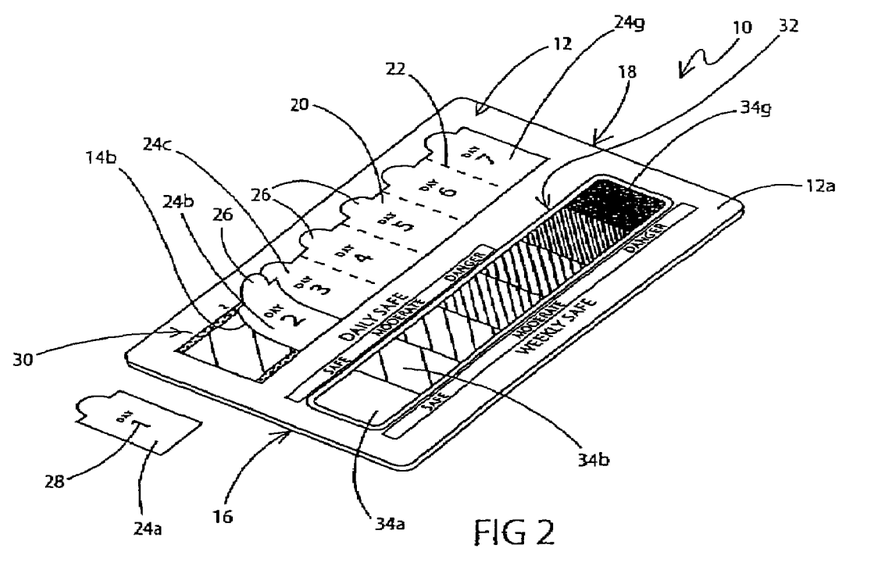
FIG. 2 is a front perspective view of the monitoring device of FIG. 1, with the protective strip for day 1 removed therefrom.

So, as shown in FIG. 2, the color change on day 1 as indicated by region 14a, when compared with indicators 34 on scale 32, most closely represents indicator 34b. When reference is made to the first key 36, it will be seen that indicator 34b falls within a zone between the "Safe" and "Moderate" first characters of key 36. Consequently, the monitoring individual knows that they are still within a safe range of UVR exposure for that day but should make plans to go indoors shortly.

Figure 5:
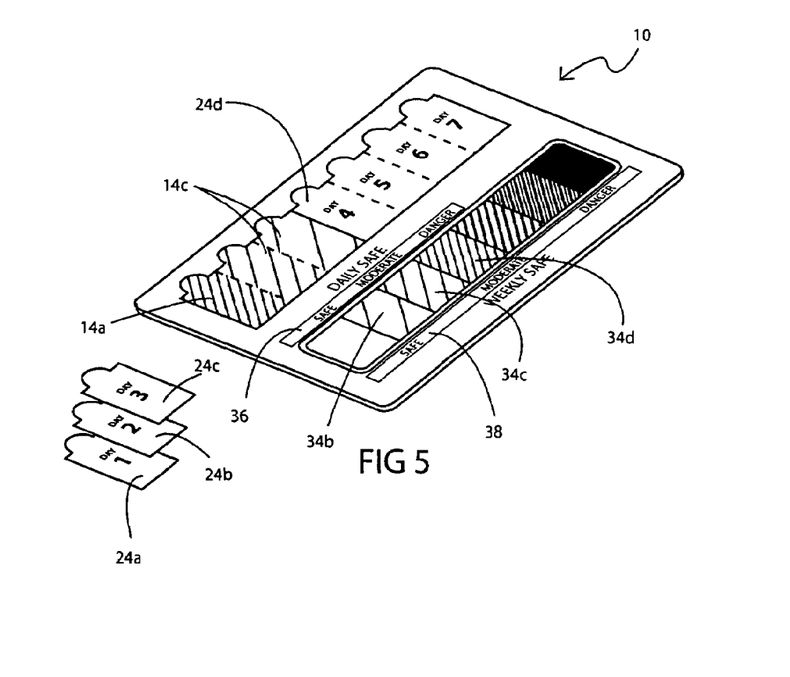
FIG. 5 is a perspective view of the monitoring device shown after a period of three days use.
Figure 6:
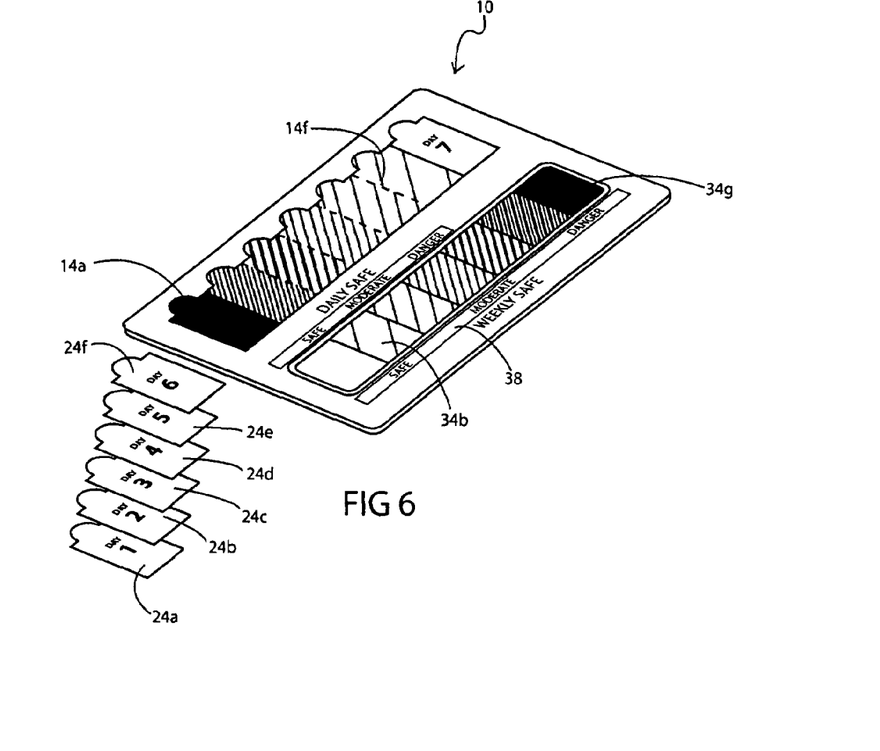
FIG. 6 is a perspective view of the monitoring device shown after a period of six days use.

One will appreciate that while an individual may be exposed to a moderate amount of UVR in a single day, over the course of a period of several days that exposure is cumulative and may be higher than desired. It is another specific feature of the present invention to provide a means for measuring cumulative exposure to UVR over a period of several days, in this instance one week. This is accomplished by progressively removing segments 24 of the cover tape 20 to expose additional regions of the UVR strip 14 as illustrated in FIGS. 2, 5 and 6. It will be understood that the UVR sensitive material used in strip 14 is of a type that maintains the change in color that occurred over the first day and does not revert back to its original state if removed from exposure to sunlight overnight, for example. The UVR sensitive material, however, does continue to change color when exposed for an additional period of time, such as if card 12 is exposed to the sun on day 2. So, if the group of individuals from day 1 (as represented by card 12 of FIG. 2) returns to the beach on day 2, the monitoring individual will remove section 46b (FIG. 4) of paper strip 42 to expose a second region 40b of adhesive layer 40. This second region 40b, in conjunction with any adhesive properties remaining from first region 40a, is used to secure card 12 to an appropriately positioned and exposed surface. The monitoring individual also removes second segment 24b of cover tape 20 to expose a second region 14b of UVR sensitive strip 14. At this stage, both the first and second regions 14a, 14b of strip 14 are exposed to UVR. Although not illustrated in these figures, it will be understood that the color change in first region 14a indicates the cumulative exposure to UVR over both day 1 and day 2. The color change in second region 14b indicates the exposure to UVR for day 2 only.

Similarly, as represented by FIG. 4, when the group returns to play in the sun on day 3, the monitoring individual will remove section 46c of paper strip 42 to expose a third region of adhesive layer 40. The third segment 24c of cover tape 20 is removed to expose a third region 14c of strip 14. The color change in first region 14a indicates the cumulative exposure to UVR over day 1, day 2 and day 3. The color change in second region 14b represents the cumulative exposure to UVR for day 1 and day 2, and the color change in third region 14c indicates the UVR exposure for day 3 only. The monitoring individual will then compare the color change in region 14c with scale 32 and first characters of first key 36 to determine if the UVR exposure for day 3 is low, moderate or high. As illustrated in FIG. 5, the color change in 14c most closely resembles indicator 34b. When indicator 34b is compared to first characters of first key 36, the region falls between the "Safe" and "Moderate" zones. The monitoring individual therefore knows their exposure to UVR for that day, day 3, is not too high and is safe. The monitoring individual also compares first region 14a with scale 32 and second characters of second key 38. It will be seen that region 14a most closely resembles indicator 34d and when this indicator 34d compared with second key 38 it falls in the range of the "Moderate" second character. The monitoring individual therefore knows that their weekly exposure is satisfactory and they can safely continue to be in the sun over the next few days.

FIG. 6 represents the monitoring device 10 after six days exposure to the sun. The color change in region 14a represents the cumulative exposure to UVR over days 1 to 6, and the color change in region 14f represents the exposure to UVR on day 6 only. When region 14f is compared with scale 32 and first characters of first key 36, it will be seen that the region 14f most closely resembles region 34b. Using the daily first key 36, the monitoring individual will see that their exposure for day 6 is between "Safe" and "Moderate". Region 14a is then compared to scale 32 and second characters of second key 38. Region 14a most closely resembles indicator 34g of scale 32. When indicator 34g is compared with second key 38, it will be seen that the region is in the "Danger" zone. Consequently, the monitoring individual is able to determine that too much exposure to UVR has occurred over the six day period and that the group or individual should not go out into the sun on the seventh day of that week.

Once all of the segments 24a-24g of cover tape 20 have been removed or maximum exposure to UVR as indicated by card 12 has been reached, card 12 may be disposed of. If the vacation extends for a period longer than one week, a second card can be utilized for monitoring exposure to UVR for the second week. The monitoring individual can retain the first card 12 and use both cards for the second week so that the first exposed section 14a of strip 14 continues to monitor total UVR exposure over the entire vacation. If the maximum recorded level of UVR exposure on scale 32 is reached prior to the end of the vacation, the monitoring individual would be advised to take steps to avoid outdoor activities for the remainder of the vacation.

FIGS. 7-10 show a second embodiment of a monitoring device in accordance with the present invention and generally indicated at 110. Monitoring device 110 comprises a snap bracelet 112 that is designed to be snap-fittingly engaged around the wrist 113 of an individual. Snap bracelet 112 is made from a narrow thin piece of spring steel and is coiled during manufacture so that it has a memory. During manufacture, a small radius is formed across the bracelet's width that can keep the strip from coiling until the radius is compromised (i.e., flattened) and allows the curling to start around the individual's wrist. Bracelet 112 is also easy to remove if the individual is going to take part in an activity and can be left wrapped around the arm of a beach chair to keep its exposure correct. It is easily placed around the wrist once again when the individual is finished with their activity.

Figure 7:
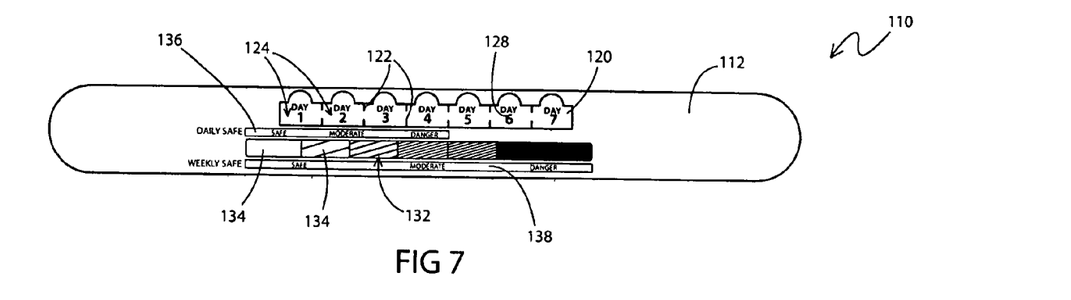
FIG. 7 is a front view of a second embodiment of an ultraviolet radiation monitoring device in accordance with the present invention shown in an unused stated.
Figure 8:
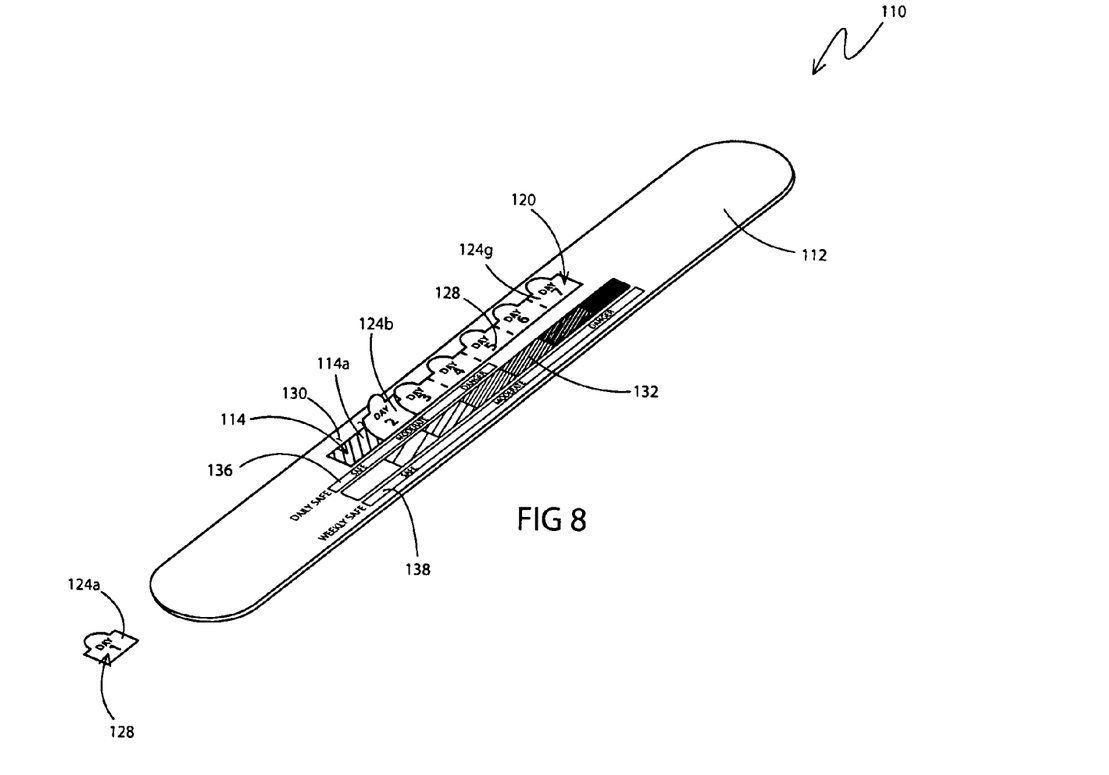
FIG. 8 is a front perspective view of the monitoring device of FIG. 7 with the protective strip for day 1 removed.

Bracelet 112 includes a strip 114 of an adhesive-backed ultraviolet sensitive material that is applied to a central region of bracelet 112. A cover tape 120 is applied over the UV sensitive strip 114 and is provided with a plurality of lines of perforations 122 that effectively divide strip 120 into a plurality of individual segments 124, such as segments 124a, 124b-124g. As with the previous embodiment, an adhesive is applied to an inner surface of cover tape 120 in such a manner that each segment 124 is individually secured to bracelet 112. Segments 124 are also each provided with a non-adhesive tab 126 that enables it to be individually detached from strip 120. and removed from card 12. Segments 124 are also preferably marked with indicators 128 which identify the individual time periods represented by segments 124. Bracelet 112 preferably is also marked with indicators 130 that correspond to the indicators 128 on the individual segments. As with the previous embodiment, bracelet 112 is also provided with a graduated exposure scale 132 that includes individual indicators 134 that indicate a color change commensurate with the differing levels of UVR exposure. A first set of characters 136 represent daily exposure levels and a second set of characters 138 represent cumulative exposure levels.

Figure 9:
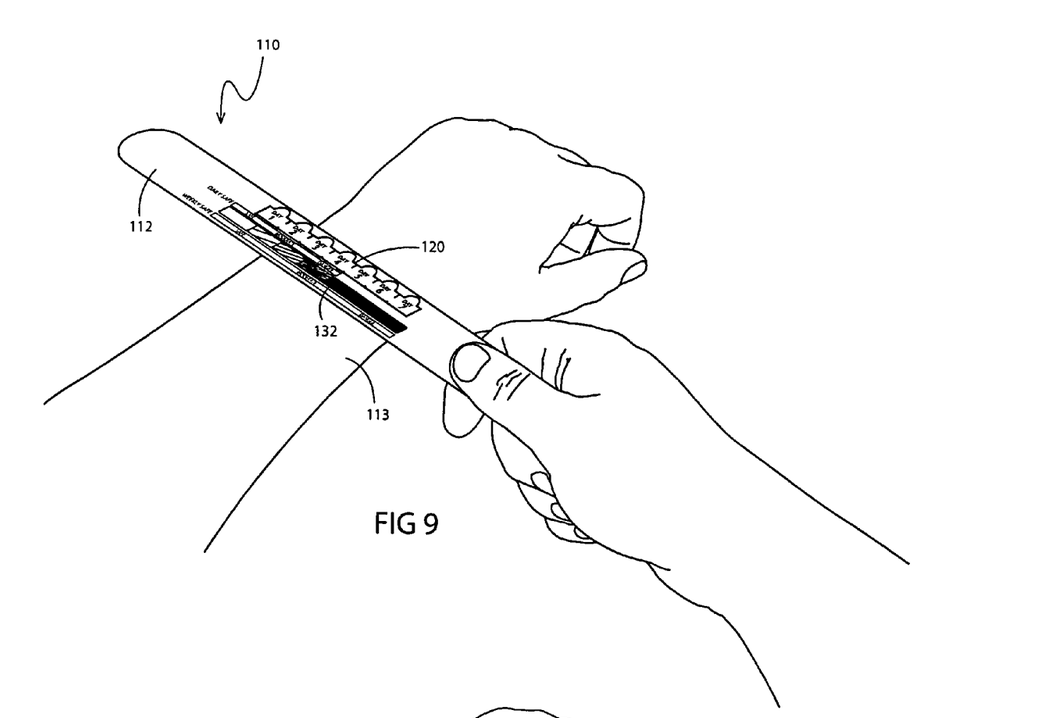
FIG. 9 is a perspective view of the monitoring device of FIG. 7 being positioned for use on a user's wrist.
Figure 10:
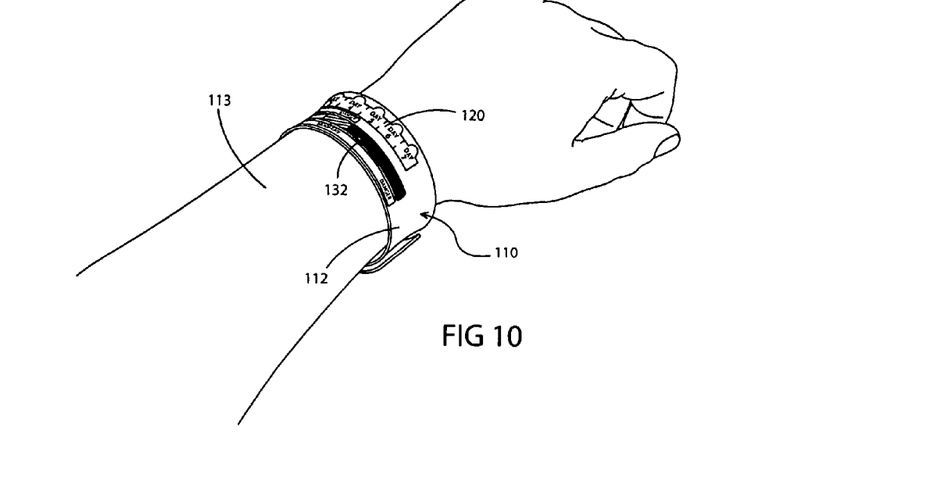
FIG. 10 is a perspective view of the monitoring device of FIG. 7 in use on a user's wrist.

The monitoring device 112 is used in essentially the same manner as card 12, except that the monitoring individual snap fits bracelet 112 onto their wrist 113 (FIGS. 9 and 10). The individual also needs to take care that adhesive strip 114 continually faces the sun, so the bracelet's orientation on the wrist 113 may need to be adjusted a number of times during outdoor activities to correct its orientation. Once again, segments 124 of cover tape 120 are progressively removed over the course of a week and the exposure level indicated by the first section 114a is used to determine cumulative exposure to UVR using second characters 138 and scale 132.

It will be understood that while the UVR sensitive material 14 has been shown in the attached figures as a strip of material, the UVR sensitive material may be applied to either card 12 or bracelet 112 as discrete dots or other shaped members, without departing from the spirit of the present invention. Similarly, the perforated segments 24, 124 of strip 20, 120 may be discrete and separate paper cover segments that are not attached to each other and are individually applied over discrete pieces of UVR sensitive materials, without departing from the spirit of the present invention. It will further be understood that instead of a single continuous strip 14 of UVR material being applied to card 12, a first substantially continuous strip may be applied in a first region of card 12 or bracelet 112 for tracking exposure on a daily basis in the same manner shown in FIG. 1. However, a second and separate strip of UVR sensitive material may be applied in a different region of card 12 or bracelet 112, such as adjacent the high exposure end of scale 32 to make it easier to determine if the individual has been exposed to maximum level of UVR indicated on the scale.

Furthermore, card 12 may be otherwise attached to a surface, such as by a lanyard 50 (FIG. 3A) received through an aperture 52 in card 12 or by a magnetic strip 54 (FIG. 3B) applied to back surface 12b thereof.

It will further be understood that the card 12 and bracelet 112 are merely representations of a possible medium or base upon which the UVR sensitive strip 14 and related components may be applied. Any other suitable base or medium, such as a container for sunscreen, can be used without departing from the spirit of the present invention.

It will also be understood that the UVR sensitive strip 114 used in this monitoring device 10 may be of any type, including UVR sensitive materials that can have sunscreen applied over them and materials that are manufactured to record UVR exposure for different skin tones.

It will further be understood that each of the characters 28 marked upon segments 24 represents a period of time, that time period may be one hour, several hours, a day or any other predetermined period. The characters marked across all of the segments 24 of tape 20 represent incremental increases in a period of time over which the device 10 is designed to be used.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of the invention are an example and the invention is not limited to the exact details shown or described.

The invention claimed is:

1. A disposable device for monitoring cumulative exposure to ultraviolet radiation (UVR) over several successive periods of time; said device comprising:
    a single base having an upper surface and a lower surface;
    a single area of UVR sensitive material applied to the upper surface of the base; said UVR sensitive material formulated to undergo a visible change upon exposure to UVR;
    a protective covering secured to the upper surface of the base and applied over the single area of UVR sensitive material; wherein the protective covering comprises:
        a plurality of coplanar segments disposed laterally adjacent each other, each segment being disposed over one of a plurality of discrete regions of said single area of UVR sensitive material and being successively individually removable from the protective covering to expose successive regions of the single area of UVR sensitive material to UVR; and
    an exposure scale disposed on the base; whereby the change in the UVR sensitive material in each discrete region is comparable with the scale to determine a level of exposure to UVR.

2. The monitoring device as defined in claim 1, wherein the protective covering comprises a single strip of protective tape that is divided into the plurality of segments by spaced apart lines of perforations; where said perforations permit each segment to be individually separated from the strip.

3. The monitoring device as defined in claim 2, wherein each of the segments has an interior surface upon which an adhesive is applied, said adhesive being positioned to engage the base but not the UVR sensitive material.

4. The monitoring device as defined in claim 3, wherein each of the segments includes an adhesive free tab extending outwardly away therefrom.

5. The monitoring device as defined in claim 2, wherein each of the segments includes one of a first plurality of characters marked upon an external surface thereof; each of said characters representing a period of time.

6. The monitoring device as defined in claim 5, wherein the first plurality of characters marked across the plurality of segments represents an incremental series of periods of time over which the device is to be used.

7. The monitoring device as defined in claim 5, further comprising a second plurality of characters marked on the base adjacent the UVR sensitive material, each of the second characters being associated with one of the segments having one of the first characters thereon.

8. The monitoring device as in claim 7, wherein each of the second plurality of characters is marked on the base in a position that causes it to be disposed beneath a tab on one of the segments.

9. The monitoring device as in claim 1, wherein the exposure scale is an achievable color range for the UVR sensitive material after exposure to UVR.

10. The monitoring device as in claim 9, further comprising a first key provided on the base adjacent the exposure scale, said first key being adapted to work with the scale to indicate a level of exposure of the device to UVR over a single period of time.

11. The monitoring device as in claim 10, further comprising a second key provided on the base adjacent the exposure scale and the first key, said second key being adapted to work with the scale to indicate a cumulative exposure of the device to UVR over several cumulative periods of time.

12. The monitoring device as defined in claim 1, wherein the base further includes a connector that is adapted to secure the base to a surface that is positioned for UVR exposure.

13. The monitoring device as defined in claim 12, wherein the connector comprises one of an adhesive layer, a lanyard and a magnetic strip.

14. The monitoring device as defined in claim 13, wherein the connector is an adhesive layer and the base further includes a protective strip applied over the adhesive layer.

15. The monitoring device as in claim 14, wherein the protective strip includes a plurality of perforations which divide the protective strip into individually separable sections that are individually removable to progressively reveal a portion of said adhesive layer for connection of the base to the surface.

16. The monitoring device as defined in claim 1, wherein the base comprises one of a card and a snap bracelet.

17. The monitoring device as defined in claim 1, wherein the UVR sensitive material is one that undergoes an irreversible color change when exposed to UVR.

18. A method of monitoring exposure to UVR comprising:
securing a monitoring device to a surface;
removing a first cover segment from the monitoring device to reveal a first section of a UVR sensitive material thereunder;
permitting the monitoring device to be exposed to UVR for a specified first period of time such that a visible change occurs in the UVR sensitive material in the first section;
comparing the change in the UVR sensitive material in the first section to a graduated scale on the monitoring device after the first period of time;
referencing a first key proximate the graduated scale to determine the extent of UVR exposure during the first period of time;
removing a second cover segment from the monitoring device to reveal a second section of UVR sensitive material thereunder, where the second section is disposed laterally adjacent the first section;
permitting the monitoring device to be exposed to UVR for a specified second period of time such that a visible change occurs in the UVR sensitive material in each of the first and second sections;
comparing the change in the UVR sensitive material in the second section to the graduated scale on the monitoring device after the second period of time;
comparing the change in the UVR sensitive material in the second section to the first key to determine the extent of UVR exposure during the second period; and
comparing the change in the UVR sensitive material in the first section to the second key to determine the cumulative extent of UVR exposure over both of the first and second periods of time.

19. A method of monitoring exposure to UVR comprising:
securing a monitoring device to a surface;
removing a first cover segment from the monitoring device to reveal a first section of UVR sensitive material thereunder;
comparing a change in the UVR sensitive material in the first section to a graduated scale on the monitoring device after a specified first period of time; and
referencing a first key proximate the graduated scale to determine extent of UVR exposure of the first period of time;
removing a second cover segment from the monitoring device to reveal a second section of UVR sensitive material thereunder;
comparing a change in the UVR sensitive material in the second section to the graduated scale on the monitoring device after a specified second period of time; and
referencing the first key proximate the graduated scale to determine the extent of UVR exposure over the second period of time;
comparing a change in the UVR sensitive material in the first section to the graduated scale on the monitoring device after the second period of time;
referencing a second key proximate the graduated scale to determine the cumulative extent of UVR exposure over a combination of the first and second period of time.

20. A disposable device for monitoring exposure to ultraviolet radiation (UVR); said device comprising:
a base having an upper surface and a lower surface;
a single strip of UVR sensitive material applied to the upper surface of the base; said UVR sensitive material formulated to undergo a visible change upon exposure to UVR;
a protective tape secured to the base and disposed to cover the strip of UVR sensitive material, said tape including a plurality of perforations that divide the tape into sections; each section being individually removable from the tape after specified periods of time so as to progressively expose regions of said UVR sensitive material to UVR;
an exposure scale disposed on the base adjacent the strip of UVR sensitive material; said scale permitting monitoring of the change in the UVR sensitive material over a single period of time and over several cumulative periods of time.

* * * * *